US009511028B2

(12) United States Patent
Chen et al.

(10) Patent No.: US 9,511,028 B2
(45) Date of Patent: Dec. 6, 2016

(54) ORALLY DISINTEGRATING TABLET

(71) Applicant: JOHNSON & JOHNSON CONSUMER INC., Skillman, NJ (US)

(72) Inventors: Jen-Chi Chen, Morrisville, PA (US); Kenneth Day, Harleysville, PA (US); Christopher E. Szymczak, Marlton, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 447 days.

(21) Appl. No.: 13/803,527

(22) Filed: Mar. 14, 2013

(65) Prior Publication Data

US 2013/0295175 A1 Nov. 7, 2013

Related U.S. Application Data

(60) Provisional application No. 61/640,910, filed on May 1, 2012.

(51) Int. Cl.

| A61K 9/00 | (2006.01) |
|---|---|
| A61K 9/20 | (2006.01) |
| A61K 31/167 | (2006.01) |
| A61K 31/426 | (2006.01) |
| A61K 31/7004 | (2006.01) |

(52) U.S. Cl.
CPC ............ *A61K 9/2081* (2013.01); *A61K 9/0056* (2013.01); *A61K 9/2018* (2013.01); *A61K 9/2095* (2013.01); *A61K 31/167* (2013.01); *A61K 31/426* (2013.01); *A61K 31/7004* (2013.01)

(58) Field of Classification Search
CPC ..................... A61K 9/0056; A61K 9/2018
See application file for complete search history.

(56) References Cited

U.S. PATENT DOCUMENTS

| 2,183,053 A | 12/1939 | Taylor |
|---|---|---|
| 2,887,437 A | 5/1959 | Klioze et al. |
| 3,071,470 A | 1/1963 | Bishop |
| 3,337,116 A | 8/1967 | Nowak |
| 3,586,066 A | 6/1971 | Brown |
| 3,670,065 A | 6/1972 | Eriksson et al. |
| 3,885,026 A | 5/1975 | Heinemann et al. |
| 4,158,411 A | 6/1979 | Hall et al. |
| 4,173,626 A | 11/1979 | Dempski et al. |
| 4,230,693 A | 10/1980 | Izzo et al. |
| 4,238,431 A | 12/1980 | Stuben et al. |
| 4,260,596 A | 4/1981 | Mackles |
| 4,268,238 A | 5/1981 | Marc |
| 4,268,465 A | 5/1981 | Suh et al. |
| 4,327,076 A | 4/1982 | Puglia et al. |
| 4,396,564 A | 8/1983 | Stuben et al. |
| 4,398,634 A | 8/1983 | McClosky |
| 4,508,740 A | 4/1985 | McSweeney |
| 4,526,525 A | 7/1985 | Oiso et al. |
| 4,590,075 A | 5/1986 | Wei et al. |
| 4,609,543 A | 9/1986 | Morris et al. |
| 4,642,903 A | 2/1987 | Davies |
| 4,684,534 A | 8/1987 | Valentine |
| 4,758,439 A | 7/1988 | Godfrey |
| 4,762,719 A | 8/1988 | Forester |
| 4,777,050 A | 10/1988 | Vadino |
| 4,824,681 A | 4/1989 | Schobel et al. |
| 4,828,845 A | 5/1989 | Zamudio-Tena et al. |
| 4,832,956 A | 5/1989 | Gergely et al. |
| 4,851,226 A | 7/1989 | Julian et al. |
| 4,857,331 A | 8/1989 | Shaw et al. |
| 4,863,742 A | 9/1989 | Panoz et al. |
| 4,906,478 A | 3/1990 | Valentine et al. |
| 4,979,720 A | 12/1990 | Robinson |
| 4,980,170 A | 12/1990 | Schneider et al. |
| 4,984,240 A | 1/1991 | Keren-Zvi et al. |
| 4,994,260 A | 2/1991 | Kallstrand et al. |
| 5,013,557 A | 5/1991 | Tai |
| 5,046,618 A | 9/1991 | Wood |
| 5,064,656 A | 11/1991 | Gergely et al. |
| 5,073,374 A | 12/1991 | McCarty |
| 5,075,114 A | 12/1991 | Roche |
| 5,082,436 A | 1/1992 | Choi et al. |
| 5,109,893 A | 5/1992 | Derby |
| 5,112,616 A | 5/1992 | McCarty |

(Continued)

FOREIGN PATENT DOCUMENTS

| CN | 1119934 A | 4/1996 |
|---|---|---|
| CN | 1141589 A | 1/1997 |

(Continued)

OTHER PUBLICATIONS

Jones, P. L. et al, "Dielectric Drying", Drying Technology, 14(5), 1996, p. 1063-1098.
Guo, et al., Temperature and Moisture Dependent Dielectric Properties of Legume Flour Associated with Dielectric Heating, LWT Food Science and Technology 43, 2010, p. 193-201.
Katsuki, et al., Novel Energy-Saving Materials for Microwave Heating, Chem Mater. 2008, 20, p. 4803-4807.
Radio-Frequency Heating of Plastics, TechCommentary, vol. 4, No. 2, 1987, p. 1-4.
Jones, P. L., High Frequency Dielectric Heating in Paper Making, Drying Technology, 4(2), 1986, p. 217-244.
What is R.F. Heat Sealing?, Dielectric Sealing Service, Inc., 2007, p. 1-6.

(Continued)

*Primary Examiner* — Michael B Pallay

(57) ABSTRACT

The present invention features a tablet containing at least one first material, at least one second material, and at least one pharmaceutically active agent, wherein:

(a) the first material is a dielectric water-containing material (i) containing from about 1 to about 5 percent, by weight, of bound water and (ii) having a dielectric loss, when measured at a density of between 0.15 and 0.5 g/cc, of from about 0.05 to about 0.7; and (b) the second material (i) having a water solubility from about 20 to about 400 g per 100 g of water at 25° C., (ii) having a dielectric loss, when measured at a density between 0.5 and 1 g/cc, of less than about 0.05.

15 Claims, No Drawings

(56) References Cited

U.S. PATENT DOCUMENTS

| | | |
|---|---|---|
| 5,126,151 A | 6/1992 | Bodor et al. |
| 5,134,260 A | 7/1992 | Piehler et al. |
| 5,139,407 A | 8/1992 | Kim et al. |
| 5,178,878 A | 1/1993 | Wehling et al. |
| 5,215,755 A | 6/1993 | Roche et al. |
| 5,223,264 A | 6/1993 | Wehling et al. |
| 5,262,171 A | 11/1993 | Login et al. |
| 5,275,822 A | 1/1994 | Valentine et al. |
| 5,286,497 A | 2/1994 | Hendrickson et al. |
| 5,304,055 A | 4/1994 | Van Lengerich et al. |
| 5,320,848 A | 6/1994 | Geyer et al. |
| 5,330,763 A | 7/1994 | Gole et al. |
| 5,464,632 A | 11/1995 | Cousin et al. |
| 5,489,436 A | 2/1996 | Hoy et al. |
| 5,501,858 A | 3/1996 | Fuisz |
| 5,501,861 A | 3/1996 | Makino et al. |
| 5,503,846 A | 4/1996 | Wehling et al. |
| 5,558,880 A | 9/1996 | Gole et al. |
| 5,558,899 A | 9/1996 | Kuzee et al. |
| 5,560,963 A | 10/1996 | Tisack |
| 5,587,172 A | 12/1996 | Cherukuri et al. |
| 5,587,179 A | 12/1996 | Gergely et al. |
| 5,607,697 A | 3/1997 | Alkire et al. |
| 5,622,719 A | 4/1997 | Myers et al. |
| 5,631,023 A | 5/1997 | Kearney et al. |
| 5,635,210 A | 6/1997 | Allen, Jr. et al. |
| 5,648,093 A | 7/1997 | Gole et al. |
| 5,653,993 A | 8/1997 | Ghanta et al. |
| 5,662,849 A | 9/1997 | Bogne et al. |
| 5,672,364 A | 9/1997 | Kato et al. |
| 5,720,974 A | 2/1998 | Makino et al. |
| 5,814,339 A | 9/1998 | Prudhoe |
| 5,886,081 A | 3/1999 | Sternowski |
| 5,912,013 A | 6/1999 | Rudnic et al. |
| 5,939,091 A | 8/1999 | Eoga et al. |
| 5,997,905 A | 12/1999 | McTeigue et al. |
| 6,024,981 A | 2/2000 | Khankari et al. |
| 6,060,078 A | 5/2000 | Lee |
| 6,103,260 A | 8/2000 | Luber et al. |
| 6,224,905 B1 | 5/2001 | Lawrence et al. |
| 6,228,398 B1 | 5/2001 | Devane et al. |
| 6,258,381 B1 | 7/2001 | Luber et al. |
| 6,270,805 B1 | 8/2001 | Chen et al. |
| 6,277,409 B1 | 8/2001 | Luber et al. |
| 6,284,270 B1 | 9/2001 | Lagoviyer et al. |
| 6,287,596 B1 | 9/2001 | Murakami et al. |
| 6,316,026 B1 | 11/2001 | Tatara et al. |
| 6,322,819 B1 | 11/2001 | Burnside et al. |
| 6,328,994 B1 | 12/2001 | Shimizu et al. |
| 6,465,010 B1 | 10/2002 | Lagoviyer et al. |
| 6,499,984 B1 | 12/2002 | Ghebre-Sellassie et al. |
| 6,569,463 B2 | 5/2003 | Patel et al. |
| 6,589,554 B1 | 7/2003 | Mizumoto et al. |
| 6,612,826 B1 | 9/2003 | Bauer et al. |
| 6,649,888 B2 | 11/2003 | Ryan et al. |
| 6,753,009 B2 | 6/2004 | Luber et al. |
| 6,767,200 B2 | 7/2004 | Sowden et al. |
| 6,814,978 B2 | 11/2004 | Bunick et al. |
| 6,932,979 B2 | 8/2005 | Gergely |
| 7,070,825 B2 | 7/2006 | Ndife et al. |
| 7,132,072 B2 | 11/2006 | Ozeki et al. |
| 7,157,100 B2 | 1/2007 | Doshi et al. |
| 7,625,622 B2 | 12/2009 | Teckoe et al. |
| 8,127,516 B2 | 3/2012 | Lee et al. |
| 8,313,768 B2 | 11/2012 | Kriksunov et al. |
| 8,343,533 B2 | 1/2013 | Chen et al. |
| 2001/0033831 A1 | 10/2001 | Chow et al. |
| 2002/0012701 A1 | 1/2002 | Kolter et al. |
| 2002/0018800 A1 | 2/2002 | Pinney et al. |
| 2002/0079121 A1 | 6/2002 | Ryan et al. |
| 2002/0122822 A1* | 9/2002 | Bunick et al. ............... 424/464 |
| 2003/0021842 A1 | 1/2003 | Lagoviyer et al. |
| 2003/0068367 A1 | 4/2003 | Sowden et al. |
| 2003/0068373 A1 | 4/2003 | Luber et al. |
| 2003/0161879 A1 | 8/2003 | Ohmori et al. |
| 2003/0175339 A1 | 9/2003 | Bunick et al. |
| 2003/0194442 A1 | 10/2003 | Guivarch et al. |
| 2003/0224044 A1 | 12/2003 | Weibel |
| 2003/0228368 A1 | 12/2003 | Wynn et al. |
| 2004/0115305 A1 | 6/2004 | Andersen et al. |
| 2004/0137057 A1 | 7/2004 | Sowden et al. |
| 2004/0156902 A1 | 8/2004 | Lee et al. |
| 2004/0191499 A1 | 9/2004 | Hallett et al. |
| 2005/0019407 A1 | 1/2005 | Sowden et al. |
| 2005/0138899 A1 | 6/2005 | Draisey et al. |
| 2005/0142188 A1 | 6/2005 | Gilis et al. |
| 2005/0186274 A1 | 8/2005 | Kohlrausch |
| 2006/0034927 A1 | 2/2006 | Casadevall et al. |
| 2006/0134195 A1 | 6/2006 | Fu et al. |
| 2007/0071806 A1 | 3/2007 | McCarty |
| 2007/0184111 A1 | 8/2007 | Harris et al. |
| 2007/0196477 A1 | 8/2007 | Witham et al. |
| 2007/0281009 A1 | 12/2007 | Kamisono et al. |
| 2008/0286340 A1 | 11/2008 | Andersson et al. |
| 2009/0060983 A1 | 3/2009 | Bunick et al. |
| 2009/0092672 A1 | 4/2009 | Venkatesh et al. |
| 2009/0110716 A1 | 4/2009 | Bunick et al. |
| 2009/0110717 A1 | 4/2009 | Singh et al. |
| 2009/0311320 A1 | 12/2009 | Oury et al. |
| 2010/0016348 A1 | 1/2010 | Bunick et al. |
| 2010/0016451 A1 | 1/2010 | Bunick et al. |
| 2010/0021507 A1 | 1/2010 | Bunick et al. |
| 2011/0068511 A1 | 3/2011 | Sowden et al. |
| 2011/0070170 A1 | 3/2011 | Koll et al. |
| 2011/0070286 A1 | 3/2011 | Hugerth et al. |
| 2011/0070301 A1 | 3/2011 | Luber et al. |
| 2011/0071184 A1 | 3/2011 | Bunick et al. |
| 2011/0071185 A1 | 3/2011 | Bunick et al. |
| 2011/0318411 A1* | 12/2011 | Luber et al. ............... 424/464 |
| 2011/0319441 A1 | 12/2011 | Szymczak et al. |
| 2011/0319492 A1 | 12/2011 | Luber et al. |
| 2012/0022170 A1 | 1/2012 | Bunick et al. |

FOREIGN PATENT DOCUMENTS

| | | |
|---|---|---|
| CN | 1498080 A | 5/2004 |
| CN | 1805735 A | 7/2006 |
| CN | 101052373 A | 10/2007 |
| EP | 0 070 127 | 1/1983 |
| EP | 0192460 B1 | 8/1986 |
| EP | 0 416 791 A2 | 3/1991 |
| EP | 0829341 | 3/1998 |
| EP | 1974724 A2 | 10/2008 |
| EP | 2308511 B1 | 12/2012 |
| GB | 772 315 | 4/1957 |
| GB | 1 097 207 | 12/1967 |
| GB | 1538280 A | 1/1979 |
| JP | 59 067006 A | 4/1984 |
| JP | 62/205009 | 9/1987 |
| JP | 0649482 B | 6/1994 |
| JP | 1999033084 A | 2/1999 |
| JP | 2010531350 A | 9/2010 |
| RU | 2082436 C | 6/1997 |
| RU | 2233854 C | 8/2004 |
| SU | 862816 A | 9/1981 |
| SU | 925673 A | 5/1982 |
| SU | 1632629 A | 3/1991 |
| WO | WO 91/12881 | 9/1991 |
| WO | WO 92/04920 A | 4/1992 |
| WO | WO 92/06679 | 4/1992 |
| WO | WO 93/13758 A1 | 7/1993 |
| WO | WO 94/06416 | 3/1994 |
| WO | WO 95/09044 A1 | 4/1995 |
| WO | WO 97/38679 A2 | 10/1997 |
| WO | WO 98/32426 A1 | 7/1998 |
| WO | WO 99/17771 | 4/1999 |
| WO | WO 99/44580 A1 | 9/1999 |
| WO | WO 00/004281 | 1/2000 |
| WO | WO 02/47607 | 6/2002 |
| WO | WO 03/059327 A1 | 7/2003 |
| WO | WO 2003/061399 A1 | 7/2003 |
| WO | WO 03/101431 A1 | 12/2003 |
| WO | WO 2004/000197 A2 | 12/2003 |
| WO | WO 2004/046296 A1 | 6/2004 |

(56) References Cited

FOREIGN PATENT DOCUMENTS

| WO | WO 2004/100857 A2 | 11/2004 |
|---|---|---|
| WO | WO 2004/110413 A | 12/2004 |
| WO | WO 2006/018074 A1 | 2/2006 |
| WO | WO 2006/127618 | 11/2006 |
| WO | WO 2007/042153 A1 | 4/2007 |
| WO | WO 2007/104574 A2 | 9/2007 |
| WO | WO 2007/125545 A2 | 11/2007 |
| WO | WO 2007/141328 | 12/2007 |
| WO | WO 2008/005318 A2 | 1/2008 |
| WO | WO 2008/015221 A2 | 2/2008 |
| WO | WO 2007/125545 A2 | 11/2008 |
| WO | WO 2009/022670 A | 2/2009 |
| WO | WO 2009/032655 | 3/2009 |
| WO | WO 2009/037319 A2 | 3/2009 |
| WO | WO 2009/080022 A1 | 7/2009 |
| WO | WO 2010/058218 A1 | 5/2010 |
| WO | WO 2012/039788 A1 | 3/2012 |
| ZA | 8704899 | 3/1988 |

OTHER PUBLICATIONS

Broadband RF Survey Instruments, ETS•Lindgren Haladay EMF Measurement, 2002, p. 1-2.
Lamp IR Infrared Heaters: Infrared Lamps for Controlled Concentrated Heating, Research Inc., p. 1-20., Sep. 20, 2010.
Callebaut, Power Quality & Utilisation Guide, Section 7: Energy Efficiency, Mar. 2007, www.leonardo-energy.org, p. 1-9.
Shukla, et al., Mouth Dissolving Tablets I: An Overview of Formulation Technology, Sci Pharm 2009, 76: p. 309-326.
Lieberman, Herbert a. et al., "Pharmaceutical Dosage Forms—Tablets", vol. 2, $2^{nd}$ Ed. pp. 213-217; 327-329, Marcel Dekker, Inc., 1990, New York and Basel.
Lachman, Leon et al., "The Theory and Practice of Industrial Pharmacy", $3^{rd}$ Ed., Chapter 11, pp. 293-345,Lea & Febiger, 1986, Philadelphia.
McConville, J. et al., "Erosion characteristics of an erodible tablet incorporated in a time-delayed capsule device," Drug Development and Industrial Pharmacy, vol. 31, No. 1, 2005, pp. 79-89, XP008108019.
USP 23 (1995) 1216, Tablet Friability, p. 1981.
USP 24, 2000 Version, Acetaminophen, pp. 19-20 and Ibuprofen, p. 856 (1999).
USP 30-NF25, Disintegration, pp. 276-277, 2007.
USP 33—U.S. Pharmacopeia, General Chapter 701—Disintegration, 2008.
Orally Disintegrating Tablets, draft Food and Drug Administration Guidance, Apr. 2007.
Heng, Paul Wan Sia, Chem Pharm Bull, 47 (5) 633-638 (1999).
Koral, Tony, Radio Frequency Heating and Post-Baking, Biscuit World, Issue 4, vol. 7, Nov. 2004.
Dielectric Heating with Microwave Energy, Püschner MikrowellenEnergietechnik, pp. 1-4, Jun. 2007.
Amin, Avani F., Emerging Treands in the Development of Orally Disintegrating Tablet Technology, Pharmainfo.net, vol. 4, Issue 1, Jan. 26, 2006; pp. 1-30.
Matthes, R.; "Chapter 49" from website: http://www.ilo.org/safework_bookshelf/english?content&nd=857170571; made available online Oct. 12, 2004.
Google page showing the availability date of web reference U; provided Mar. 15, 2011.
Rambali, B., et al., International Journal of Pharmaceutics 220 (2001), pp. 129-140.
Radio Frequency Company, Microwave, (Feb. 19, 2004), pp. 1-2.
Int'l Search Report for Application No. PCT/US2008/081496, dated Jul. 15, 2009.
Int'l Search Report for Application No. PCT/US2008/74375, dated Nov. 17, 2008.
Int'l Search Report for Application No. PCT/US2010/049909 dated Dec. 3, 2010.
Int'l Search Report for Application No. PCT/US2010/049915 dated Mar. 25, 2011.
Int'l Search Report for Application No. PCT/US2010/049925 dated Dec. 8, 2010.
Int'l Search Report for Application No. PCT/US2010/049931 dated Jan. 7, 2011.
Int'l Search Report for Application No. PCT/US2010/049933 dated Feb. 15, 2011.
Int'l Search Report for Application No. PCT/US2010/049964 dated Dec. 30, 2010.
Int'l Search Report for Application No. PCT/US2010/049971 dated Jan. 7, 2011.
Int'l Search Report for Application No. PCT/US2011/029155 dated Jun. 28, 2011.
Int'l Search Report for Application No. PCT/US2011/029158 dated Jun. 28, 2011.
Int'l Search Report for Application No. PCT/US2011/029161 dated Jun. 28, 2011.
Int'l Search Report for Application No. PCT/US2010/049974 dated Mar. 5, 2013.
U.S. Appl. No. 13/718,357, filed Dec. 18, 2012—Pending.
U.S. Appl. No. 13/804,109, filed Mar. 14, 2013.
U.S. Appl. No. 13/804,229, filed Mar. 14, 2013.
U.S. Appl. No. 13/804,410, filed Mar. 14, 2013.
International Search Report mailed Aug. 20, 2013 for corresponding Patent Application No. PCT/US2013/039045.
International Search Report mailed Aug. 21, 2013 for corresponding Patent Application No. PCT/US2013/039061.
International Search Report mailed Jun. 8, 2013 for corresponding Patent Application No. PCT/US2013/039047.
Heng, P., et al., Melt Processes for Oral Solid Dosage Forms, Encyclopedia of Pharmaceutical Technology, vol. 4, Jan. 2, 2007, pp. 2257-2261.
International Search Report mailed Aug. 20, 2031 for Application No. PCT/US2013/039045.
International Search Report mailed Aug. 21, 2013 for Application No. PCT/US2013/039061.
European Search Report mailed Aug. 1, 2013 for Application No. E{08798740.
International Search Report mailed Nov. 7, 2013 for corresponding Application No. PCT/US2013/039040.
European Search Report mailed Aug. 1, 2013 for Application No. EP08798740.
Maltodextrin (Maltrin M580), Apr. 20, 2000, (PFormulate Excipients).
U.S. Appl. No. 11/847,444, filed Aug. 30, 2007, Bunick et al., Pending.
U.S. Appl. No. 12/570,046, filed Sep. 30, 2009, Bunick et al., Pending.
U.S. Appl. No. 60/983,973, filed Oct. 31, 2007, Bunick et al., Expired.
U.S. Appl. No. 12/260,151, filed Oct. 29, 2008, Bunick et al., Abandoned.
U.S. Appl. No. 12/566,078, filed Sep. 24, 2009, Bunick et al., Pending.
U.S. Appl. No. 12/566,096, filed Sep. 24, 2009, Bunick et al., Abandoned.
U.S. Appl. No. 61/245,315, filed Sep. 24, 2009, Sowden et al., Expired.
U.S. Appl. No. 61/255,582, filed Oct. 28, 2009, Sowden et al., Expired.
U.S. Appl. No. 61/314,629, filed Mar. 17, 2010, Kriksunov et al., Expired.
U.S. Appl. No. 61/358,167, filed Jun. 24, 2010, Luber et al., Expired.
U.S. Appl. No. 12/887,544, Sep. 22, 2010, Bunick et al., Granted.
U.S. Appl. No. 12/887,552, filed Sep. 22, 2010, Bunick et al., Pending.
U.S. Appl. No. 12/887,560, filed Sep. 22, 2010, Kriksunov et al., Granted.
U.S. Appl. No. 12/887,564, filed Sep. 22, 2010, Luber et al., Pending.
U.S. Appl. No. 12/887,569, filed Sep. 22, 2010, Sowden et al., Granted.
U.S. Appl. No. 12/887,575, filed Sep. 22, 2010, Koll et al., Granted.

(56) References Cited

OTHER PUBLICATIONS

U.S. Appl. No. 12/887,582, filed Sep. 22, 2010, Luber et al., Granted.
U.S. Appl. No. 12/887,593, filed Sep. 22, 2010, Hugerth et al., Pending.
U.S. Appl. No. 13/052,316, filed Mar. 21, 2011, Luber et al., Pending.
U.S. Appl. No. 13/052,219, Mar. 21, 2011, Sowden et al., Issued.
U.S. Appl. No. 13/052,200, Mar. 21, 2011, Luber et al., Pending.
U.S. Appl. No. 13/246,884, Sep. 28, 2011, Sowdent et al., Pending.
U.S. Appl. No. 13/718,357, Dec. 18, 2012, Koll et al., Granted.
U.S. Appl. No. 14/455,126, filed Aug. 8, 2014, Luber et al., Pending.
U.S. Appl. No. 61/640,910, filed May 1, 2012, Chen et al., Expired.
U.S. Appl. No. 61/704,767, filed Sep. 24, 2012, Chen et al., Expired.
U.S. Appl. No. 61,704,773, filed Sep. 24, 2012, Anderson et al., Expired.
U.S. Appl. No. 61/704,780, filed Sep. 24, 2012, Stuhl et al., Expired.
U.S. Appl. No. 13/803,527, filed Mar. 14, 2013, Chen et al., Pending.
U.S. Appl. No. 13/804,109, filed Mar. 14, 2013, Sowden et al., Pending.
U.S. Appl. No. 13/804,229, filed Mar. 14, 2013, Anderson et al., Pending.
U.S. Appl. No. 13/804,410, filed Mar. 14, 2013, Stuhl et al., Pending.
61/925,713, filed Jan. 10, 2014, Szymczak etal., Pending.
International search report for application PCT/US2015/010647 dated Mar. 18, 2015.
U.S. Appl. No. 14/592,176, filed Jan. 8, 2015, Szymczak et al.
U.S. Appl. No. 14/693,112, filed Apr. 22, 2015, Luber et al.

\* cited by examiner

ORALLY DISINTEGRATING TABLET

CROSS REFERENCE TO RELATED APPLICATIONS

This application claims priority of the benefits of U.S. Provisional Application Ser. No. 61/640,910 filed May 1, 2012. The complete disclosure of the aforementioned related U.S. patent application is hereby incorporated by reference for all purposes.

BACKGROUND OF THE INVENTION

Pharmaceuticals intended for oral administration are typically provided in tablet form. Tablets are swallowed whole, chewed in the mouth, or disintegrated in the oral cavity. Soft tablets that either are chewed or dissolve in the mouth are often employed in the administration of pharmaceuticals where it is impractical to provide a tablet for swallowing whole. With chewable tablets, the act of chewing helps to break up the tablet particles as the tablet disintegrates and may increase the rate of absorption by the digestive tract. Soft tablets are also advantageous where it is desirable to make a pharmaceutically active agent available topically in the mouth or throat for both local effects and/or systemic absorption. Soft tablets are also utilized to improve drug administration in pediatric and geriatric patients. Soft tablets designed to disintegrate in the mouth prior to swallowing are particularly useful for improving compliance of pediatric patients.

Generally, soft tablets are made by compaction of a blend of powdered ingredients and typically include a pharmaceutically active agent, flavoring, and/or binders. The powder blend is typically fed into the cavity of a die of a tablet press and a tablet is formed by applying pressure. Hardness of the resulting tablet is a direct function of the compaction pressure employed and the compatibility of the ingredients in the formulation. A softer tablet, having an easier bite-through, may be prepared by employing reduced compaction pressures. The resulting tablet is softer, but also more fragile, brittle, and easily chipped and disadvantageously can involve complex and costly processing steps. Examples of soft tablets designed to disintegrate in the mouth without chewing are disclosed in U.S. Pat. Nos. 5,464,632, 5,223,264, 5,178,878, 6,589,554, and 6,224,905.

Swallowable tablets have been produced utilizing a melt extrusion process, where the active ingredient is mixed with excipients, heated as a mass and extruded into preformed dies. These tablets are intended to be directly swallowed, and in some cases, have modified or sustained release properties. Examples of melt extruded tablets are disclosed in U.S. Pat. Nos. 6,387,401 and 7,022,344.

There is a need for aesthetically pleasing chewable and orally disintegrating tablets that utilize commercially efficient manufacturing methods. Orally disintegrating tablets can be prepared by compression (see, e.g., U.S. Pat. Nos. 5,223,264 and 5,178,878), but these tablets can have a high density and thus can take up to 20 to 30 seconds to fully disintegrate in the mouth. Lyophilized orally disintegrating tablets (see, e.g., U.S. Pat. Nos. 6,509,040, 5,976,577, 5,738,875, and 5,631,023) tend to be less dense and, thus, faster disintegrating. However, these tablets require a long time to make a tablet, and the process of lyophilization of the tablet formulation directly in the unit dose blister package renders a dosage form that is shaped on only one face.

The present invention relates to pharmaceutical orally disintegrating tablets ("ODTs") having properties of rapid oral disintegration, low density, and improved robustness to handling compared to those made by a similar process (i.e., US Patent Application No. 2011/0071184) as set forth herein. The improved robustness to handling (e.g., lower friability) is also enabled by the selection of particular materials to form a low density tablet with a more resilient structure that is less susceptible to friability.

SUMMARY OF THE INVENTION

In one aspect, the present invention features a tablet containing at least one first material, at least one second material, and at least one pharmaceutically active agent, wherein:

(a) the first material is a dielectric water-containing material (i) containing from about 1 to about 5 percent, by weight, of bound water and (ii) having a dielectric loss, when measured at a density of between 0.15 and 0.5 g/cc, of from about 0.05 to about 0.7;

(b) the second material (i) having a water solubility from about 20 to about 400 g per 100 g of water at 25° C. and (ii) having a dielectric loss, when measured at a density between 0.5 and 1 g/cc, of less than about 0.05;

(c) the tablet contains at least 15%, by weight, of the first material;

(d) the combined weight of the at least one first material and the at least one second material is at least 60%, by weight, of the tablet;

(e) the ratio of the at least one first material to the at least one second material is from about 20:80 to about 70:30;

(f) the tablet has a density less than about 0.8 g/cc; and (g) the tablet disintegrates in the mouth when placed on the tongue in less than about 30 seconds.

In another aspect, the present invention features a process for making such tablets comprising at least one pharmaceutically active agent, said method comprising the steps of applying energy to a powder blend comprising at least one first material, at least one second material, and said at least one pharmaceutically active agent.

In another aspect, the present invention features a tablet comprising at least one pharmaceutically active agent, wherein: (a) the pharmaceutically active agent is comprised within polymer-coated particles; (b) the tablet has a density less than about 0.8 g/cc; (c) the peak penetration resistance at the center of the major face of the tablet is from about 50 to about 600 grams; and (d) the tablet disintegrates in the mouth when placed on the tongue in less than about 15 seconds.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

As discussed above, in one aspect, the present invention features

Powder Blend

In one embodiment, the tablet is manufactured by applying energy to a powder blend containing at least one pharmaceutically active agent (as discussed herein), at least one first material (as discussed herein), at least one second material (as discussed herein), and optionally other suitable excipients. In one embodiment, the said at least one pharmaceutically active agent are contained within particles, such as polymer-coated particles. In one embodiment, the total amount of such particles, the at least one first material, and the at least one second material comprise at least 90%, by weight, of said powder blend/tablet, such as at least 95%, such as at least 98%, by weight of said powder blend/tablet.

In one embodiment, the powder blend/tablet comprises at least 60%, by weight, of said at least one first material and said at least one second material, such as at least 75%, such as at least 90%. In one embodiment, the ratio of said at least one first material to said at least one second material is from about 20:80 to about 70:30, such as from about 25:75 to about 60:40, such as about 35:65 to about 45:55.

Examples of suitable excipients include, but are not limited to, lubricants, glidants, sweeteners, flavor and aroma agents, antioxidants, preservatives, texture enhancers, colorants, and mixtures thereof. One or more of the above ingredients may be present on the same particle of the powder blend.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Examples of sweeteners for the present inventions include, but are not limited to high intensity sweeteners such as synthetic or natural sugars; artificial sweeteners such as saccharin, sodium saccharin, aspartame, acesulfame, thaumatin, glycyrrhizin, sucralose, dihydrochalcone, alitame, miraculin, monellin, and stevside.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including tobacco plant parts, e.g., genus *Nicotiana*, in amounts not contributing significantly to the level of nicotine, and ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment of the invention, the powder blend has an average particle size of less than 500 microns, such as from about 50 microns to about 500 microns, such as from about 50 microns and 300 microns. Particles in this size range are particularly useful for direct compacting processes.

In one embodiment, the powder blend is substantially free of polyethylene glycols, hydrated cellulose polymers, gums (such as xanthan gum and carrageenans), and gelatins. As used herein, what is meant by "substantially free" is less than 5%, such as less than 1%, such as less than 0.1%, such as completely free (e.g., 0%). Such a composition is advantageous for maintaining an immediate release dissolution profile, minimizing processing and material costs, and providing for optimal physical and chemical stability of the tablet.

In one embodiment, the powder blend/tablet is substantially free of directly compressible water insoluble fillers. Water insoluble fillers include but are not limited to microcrystalline cellulose, directly compressible microcrystalline cellulose, celluloses, water insoluble celluloses, starch, cornstarch and modified starches. As described in this embodiment, substantially free is less than 2 percent, e.g. less than 1 percent or none.

In one embodiment, the powder blend is substantially free of super disintegrants. Super disintegrants include cross carmellose sodium, sodium starch glycolate, and cross-linked povidone. A composition substantially free of super-disintegrants is advantageous for enhancing mouth-feel and tablet stability due to reduced water absorbance.

In one embodiment, at least 90%, by weight, of the tablet is comprised of material having a melting point greater than 60° C., such as at least 70° C., such as at least 80° C.

First Material

The powder blend/tablet of the present invention includes at least one first material which is a dielectric water-containing material (i) comprising from about 1 to about 5 percent, by weight, of bound water, such as from about 1.5 to about 3.2 percent, by weight, of bound water, such as from about 1.7 to about 3 percent, by weight of bound water and (ii) has a dielectric loss, when measured at a density of between 0.15 and 0.5 g/cc, of from about 0.05 to about 0.7, such as from about 0.1 to about 0.5, such as 0.25 to about 0.5.

In one embodiment, the first material is a starch. Examples of such starches include, but are not limited to, hydrolyzed starches such as maltodextrin and corn syrup solids. Such starches may be sourced from a variety of vegetable sources, such as grain, legume, and tuber, and examples include, but are not limited to, starches sourced from corn, wheat, rice, pea, bean, tapioca and potato.

In one embodiment, the first material when added to the powder blend has a bulk density of less than about 0.4 g/cc, such as less than about 0.3 g/cc, such as less than 0.2 g/cc.

In one embodiment, the average particle size of the first material is less than 500 microns, such as less than 150 microns.

The first material(s) may be present at level of at least about 15 percent, by weight, of the tablet, such as at least about 20 percent, such as from about 20 percent to about 45 percent of the powder blend/tablet, such as from about 20 percent to about 42 of the powder blend/tablet, such as from about 20 percent to about 40 of the powder blend/tablet.

Second Material

In one embodiment, the powder blend/tablet of the present invention includes at least one second material (i) having a water solubility from about 20 to about 400 g per 100 g of water at 25° C. and (ii) having a dielectric loss, when measured at a density between 0.5 and 1.1 g/cc, of less than about 0.05, such as less than about 0.01, such as less than 0.005, such as about 0. In one embodiment, the second material is crystalline at 25° C.

In one embodiment, the second material is a sugar or an alcohol or hydrate thereof. Examples of sugars include, but are not limited to, monosaccharides and disaccharides such as sucrose, fructose, maltose, dextrose, and lactose, and alcohols and hydrates thereof.

Examples of sugar alcohols include, but are not limited to, erythritol, isomalt, mannitol, maltitol, lactitol, sorbitol, and xylitol.

The second material(s) may be present at level of about 18 percent to about 72 percent of the powder blend/tablet, such as from about 20 percent to about 64 percent of the powder blend/tablet, such as from about 39 percent to about 56 percent of the powder blend/tablet.

Pharmaceutically Active Agent

The powder blend/tablet of the present invention includes at least one pharmaceutically active agent containing particles. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antipyretics, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole, dextansoprazole, esomeprazole, pantoprazole, rabeprazole, and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof; and pharmaceutically acceptable salts and prodrugs thereof.

Examples of muscle relaxants include, but are not limited to, cyclobenzaprine and chlorzoxazone metaxalone, orphenadrine, and methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof.

Examples of anesthetics (e.g., for the treatment of sore throat) include, but are not limited to dyclonine, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent included within the tablet is selected from phenylephrine, dextromethorphan, pseudoephedrine, acetaminophen, cetirizine, aspirin, nicotine, ranitidine, ibuprofen, ketoprofen, loperamide, famotidine, calcium carbonate, simethicone, chlorpheniramine, methocarbomal, chlophedianol, ascorbic acid, pectin, dyclonine, benzocaine and menthol, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the tablet, or may be in the form of particles, which in turn may be coated or uncoated. If the pharmaceutically active agent is in form of particles, the particles (whether coated or uncoated) typically have an average particle size of from about 1 to about 500 microns. In one embodiment, such particles are crystals having an average particle size of from about 1 to about 300 microns.

The pharmaceutically active agent may be present in pure crystal form or in a granulated form prior to the addition of the taste masking coating. Granulation techniques may be used to improve the flow characteristics or particle size of the pharmaceutically active agents to make it more suitable for compaction or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation.

If the pharmaceutically active agent has an objectionable taste, the pharmaceutically active agent may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked pharmaceutically active agents may also be employed. For example, acetaminophen particles, which are encapsulated with ethylcellulose or other polymers by a coacervation process, may be used in the present invention. Coacervation-encapsulated acetaminophen may be purchased commercially from Eurand America, Inc. (Vandalia, Ohio).

In one embodiment, the tablet incorporates modified release coated particles (e.g., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, sustained release or delayed release. In general, modified release tablets are formulated to make the active agents(s) available over an extended period of time after ingestion, which thereby allows for a reduction in dosing frequency compared to the dosing of the same active agent(s) in a conventional tablet. Modified release tablets also permit the use of active agent combinations wherein the duration of one pharmaceutically active agent may differ from the duration of another pharmaceutically active agent. In one embodiment the tablet contains one pharmaceutically active agent that is released in an immediate release manner and an additional active agent or a second portion of the same active agent as the first that is modified release.

Examples of swellable, erodible hydrophilic materials for use as a release modifying excipient for use in the modified release coating include water swellable cellulose derivatives, polyalkylene glycols, thermoplastic polyalkylene oxides, acrylic polymers, hydrocolloids, clays, and gelling starches. Examples of water swellable cellulose derivatives include sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose. Examples of polyalkylene glycols include polyethylene glycol. Examples of suitable thermoplastic polyalkylene oxides include poly(ethylene oxide). Examples of acrylic polymers include potassium methacrylatedivinylbenzene copolymer, polymethylmethacrylate, and high-molecular weight cross-linked acrylic acid homopolymers and copolymers.

Suitable pH-dependent polymers for use as release-modifying excipients for use in the modified release coating include: enteric cellulose derivatives such as hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (available from Rohm Pharma GmbH under the tradename EUDRAGIT S) and poly(methacrylic acid, methyl methacrylate) 1:1 (available from Rohm Pharma GmbH under the tradename EUDRAGIT L).

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent. In one embodiment, the coating which is used in the coated particle of the pharmaceutically active agent is substantially free of a material (such as polyethylene glycol) which melts below 85° C., in order to prevent damage to the integrity of the coating during the RF heating step.

In one embodiment, one or more pharmaceutically active agents or a portion of the pharmaceutically active agent may be bound to an ion exchange resin for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the tablet meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the tablet is released there from within 30 minutes after dosing, and for ibuprofen tablets, USP 24 specifies that in pH 7.2 phosphate buffer, using USP apparatus 2 (paddles) at 50 rpm, at least 80% of the ibuprofen contained in the tablet is released there from within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

In one embodiment, the pharmaceutically active agent(s) are comprised within polymer-coated particles (e.g., taste-masked and/or sustained release coated particles).

In one embodiment, the particles comprising the pharmaceutically active agents(s) may be present at level from about 10% to about 40%, by weight of the tablet/powder blend, such as 15% to about 35%, by weight of the tablet/powder blend, such as 20% to about 30%, by weight of the tablet/powder blend. In one embodiment, the particles comprising the pharmaceutically active agents(s) may be present at level of at least about 15%, by weight, of the powder blend/tablet, such as at least about 20%, by weight, of the powder blend/tablet.

Energy Application to Powder Blend

The process includes the step of applying energy to a powder blend for a sufficient period of time to form such tablet. While not wanting to be bound to this particular theory, it is believed that such energy heats the first material within the powder blend, releasing moisture and solubilizing at least a portion of the second material, following which the second material recrystallizes and forms the tablet. Various forms of energy may be used in the process to heat the first material. Suitable sources of energy include but are not limited to convection, radio frequency, microwave, UV light, infrared, induction, laser light, and ultrasonic sound.

In one embodiment, radiofrequency energy ("RF-energy") is used. Radiofrequency heating generally refers to heating with electromagnetic field at frequencies from about 1 MHz to about 100 MHz. In one embodiment of the present invention, the RF-energy is within the range of frequencies from about 1 MHz to about 100 MHz (e.g., from about 5 MHz to 50 MHz, such as from about 10 MHz to about 30 MHz). In one embodiment, the RF-energy is used to heat the first material. RF energy generators are well known in the art. Examples of suitable RF generators include, but are not limited to, COSMOS Model C10X16G4 (Cosmos Electronic Machine Corporation, Farmingdale, N.Y.). In one embodiment the RF energy is combined with a second source of heat including but not limited to infrared, induction, or convection heating.

In one embodiment, microwave heating generally refers to heating with electromagnetic field at frequencies from about 100 MHz to about 300 GHz. In one embodiment of the present invention, the RF-energy is within the range of frequencies from about 500 MHz to about 100 GHz (e.g., from about 1 GHz to 50 GHz, such as from about 1 GHz to about 10 GHz).

In the embodiment where the powder blend is heated utilizing RF-energy, the electrodes are incorporated into a chamber holding the powder blend (e.g., a cylinder, walled-sheet, or other chamber). In one embodiment, the chamber is constructed of a conductive metal. In one embodiment, the chamber has portions which are constructed of non-conductive, insulative material. In one embodiment, the chamber has an insert which is non-conductive where the body of the chamber is conductive. In one embodiment, the insert comprises a surface area which is less than that of the chamber. The conductive material may be comprised of any material which is conductive to RF-energy, including but not limited to aluminum, copper, iron, zinc, nickel and mixtures and alloys thereof. The non-conductive material may be comprised of a non-conductive solid material including but not limited to plastics and Teflon®. In one embodiment, the chamber has at least one electrode embedded into the walls of the cylinder or walled sheet. The electrode may be surrounded by non-conductive material wherein the electrode is the only conductive wall portion exposed to the power blend. In one embodiment, the powder blend is tamped prior to the addition of RF-energy.

In one embodiment, one chamber contains the powder blend and it is placed into a separate chamber (e.g., an oven) for the addition of energy. In another embodiment, the chamber containing the powder blend has additional heating elements incorporated into the chamber.

After the application of energy, the powder blend may optionally be cooled (e.g., actively cooled or allowed to cool) prior to forming a predetermined amount of the energy-applied powder blend into the tablet.

Examples of apparatuses useful for such application of energy are set forth in US Patent Application No. 20110068511.

Forming the Tablet

In one embodiment, to obtain desired attribute of an orally transformable tablet, the tablet's construction may be highly porous and/or have a low density (e.g., to allow the tablet to collapse in the oral cavity). Such tablets, therefore, are somewhat fragile and soft. In a preferred embodiment, a minimum or no tamping/compaction force is desired to achieve the orally transformable property (low density).

In one embodiment, the compaction step (e.g., tamping) which occurs prior to the addition of the energy utilizes a compaction force which is less than the force required to compress a chewable or swallowable tablet. In one embodiment, the compaction force is less than about 1000 pounds per square inch (e.g., less than about 500 pounds per square inch, such as less than 200 pounds per square inch, such as less than 50 pounds per square inch, such as none). In one embodiment, the energy is applied while the powder blend is under such force.

In one embodiment, the compaction step occurs in an indexed manner, where one set of tablets are compacted simultaneously, before rotating to another indexing station. In one embodiment, the compaction step occurs at a single indexing station and the application of energy occurs at a separate indexing station. In another embodiment, a third indexing station is present wherein the ejection of the tablet or multiple tablets occurs, wherein the lower forming tool is raised up through and up to the surface of the die. In another embodiment the compaction step is performed through the addition of air pressure or hydraulic cylinder to the top of the upper forming tools. In one embodiment multiple tablets are ejected simultaneously and separated from the surface of the indexing station and removed via a take-off bar.

In another embodiment, the tablet shape may be prepared by the compaction methods and apparatus described in United States Patent Application Publication No. 20040156902. Specifically, the tablet shape may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder blend recovery system to recover excess powder blend from the filters and return the powder blend to the dies.

In one embodiment, the tablet shape is prepared by the compaction methods and apparatus described in issued U.S. Pat. No. 6,767,200. Specifically, the tablet shape is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The tablet shape may have one of a variety of different shapes. For example, the tablet shape may be shaped as a polyhedron, such as a cube, pyramid, prism, or the like; or may have the geometry of a space figure with some non-flat faces, such as a cone, truncated cone, triangle, cylinder, sphere, torus, or the like. In certain embodiments, a tablet shape has one or more major faces. For example, the tablet shape surface typically has opposing upper and lower faces formed by contact with the upper and lower forming tool faces (e.g., die punches) in the compaction machine. In such embodiments, the tablet shape surface typically further includes a "belly-band" located between the upper and lower faces, and formed by contact with the die walls in the compaction machine. A tablet shape/tablet may also be a multilayer. Applicants have found that sharp edges in the tooling used to make the tablets can cause arcing, and thus more rounded edges may be needed.

In one embodiment, the method of producing the tablet shape is substantially free of the use of solvents. In this embodiment, the powder blend is substantially free of solvents, and the manufacturing process (e.g., filling process into the die) is also substantially free of solvents. Solvents may include, but are not limited to, water, organic solvents such as but not limited to alcohols, chlorinated solvents, hexanes, or acetone; or gaseous solvents such as but not limited to nitrogen, carbon dioxide or supercritical fluids.

In one embodiment a vibratory step is utilized (e.g., added after filling of the powder blend but prior to the heating or fusing step, in order to remove air from the powder blend). In one embodiment a vibration with the frequency from about 1 Hz to about 50 KHz is added with amplitude from 1 micron to 5 mm peak-to-peak to allow for the flowable powder blend to settle into the cavity of a the die platen ("forming cavity").

Multi-Layer Tablet

In certain embodiments, the tablet includes at least two layers, e.g., with different types and/or concentrations of the first or second material and/or other ingredients or different concentrations of pharmaceutically active agents. In one embodiment, the tablet includes two layers, one layer having orally disintegrating properties and another layer being chewable or swallowable. In one embodiment one layer is compacted at higher compaction force versus the other layer. In one embodiment, both layers have different amount of pharmaceutically active agents and/or other excipients. In one embodiment, all properties of the two layers are identical but the colors of the two layers are different.

Effervescent Couple

In one embodiment, the powder blend further contains one or more effervescent couples. In one embodiment, effervescent couple contains one member from the group consisting of sodium bicarbonate, potassium bicarbonate, calcium carbonate, magnesium carbonate, and sodium carbonate, and one member selected from the group consisting of citric acid, malic acid, fumaric acid, tartaric acid, phosphoric acid, and alginic acid.

In one embodiment, the combined amount of the effervescent couple(s) in the powder blend/tablet is from about 2 to about 20 percent by weight, such as from about 2 to about 10 percent by weight of the total weight of the powder blend/tablet.

Orally Disintegrating Tablet

In one embodiment, the tablet is designed to disintegrate in the mouth when placed on the tongue in less than about 60 seconds, e.g. less than about 45 seconds, e.g. less than about 30 seconds, e.g. less than about 15 seconds.

In one embodiment, the tablet meets the criteria for Orally Disintegrating Tablets (ODTs) as defined by the draft Food and Drug Administration guidance, as published in April, 2007. In one embodiment, the tablet meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP) disintegration test method for the specific medicinal substance or substances.

Tablets Coatings

In one embodiment, the tablet includes an additional outer coating (e.g., a translucent coating such as a clear coating) to help limit the friability of the tablet. Suitable materials for translucent coatings include, but are not limited to, hypromellose, hydroxypropylcellulose, starch, polyvinyl alcohol, polyethylene glycol, polyvinylalcohol and polyethylene glycol mixtures and copolymers, and mixtures thereof. Tablets of the present invention may include a coating from about 0.05 to about 10 percent, or about 0.1 to about 3 percent by weight of the total tablet.

Hardness/Density of Tablet

In one embodiment, the tablet is prepared such that the tablet is relatively soft (e.g., capable of disintegrating in the mouth or being chewed). In one embodiment, the hardness of the tablet of the present invention uses a Texture Analyzer TA-XT2i to measure the peak penetration resistance of the tablet. The texture analyzer is fitted with a flat faced cylindrical probe having a length equal to or longer than the thickness of the tablet (e.g., 7 mm) and a diameter of 0.5 mm. Tablet hardness is determined by the maximum penetration force of a probe boring through the center of the major face of the tablet, where the probe is a 0.5-mm diameter, stainless steel, cylindrical wire with a blunt end and the tablet is supported by a solid surface having a 2-mm diameter through-hole centered in a counter bore having a diameter slightly greater than that of the tablet, for example 0.51 inches for a 0.5 inch diameter tablet. The probe, tablet, counter-bore, and 2-mm through hole are all concentric to one another. The texture analyzer is employed to measure and report the force in grams as the probe moves at 0.1 millimeters per second through the tablet, until the probe passes through at least 80% of the thickness of the tablet. The maximum force required to penetrate the tablet is referred to herein as the peak resistance to penetration ("peak penetration resistance").

In one embodiment, the peak penetration resistance at the center of a major face is from about 2 grams to about 500 grams, such as from about 50 grams to about 600 grams, such as from about 100 grams to about 300 grams.

In one embodiment, the density of the tablet is less than about 0.8 g/cc, such as less than about 0.7 g/cc.

In one embodiment, the tablets have a friability of less than 10 percent, such as less than 5 percent, such as less than 1 percent. As used herein, "friability" is measured using the USP 24 NF 29 Tablet Friability (Section1216) with the modification of using 3 tablets for 10 rotations (unless otherwise noted) rather than 10 tablets for 100 rotations.

Use of Tablet

The tablets may be used as swallowable, chewable, or orally disintegrating tablets to administer the pharmaceutically active agent.

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlorphediaonol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet.

EXAMPLES

Specific embodiments of the present invention are illustrated by way of the following examples. This invention was not confined to the specific limitations set forth in these examples.

Example 1

Manufacture of Orally Disintegrating Tablet Containing Erythritol and Acetaminophen The acetaminophen powder blend for an orally disintegrating tablet, containing the ingredients of Table 1, was manufactured as follows:

TABLE 1

| a: Acetaminophen Powder Blend Formulation (30.8% APAP) | | | |
| --- | --- | --- | --- |
| Ingredient | G/Batch | mg/Tablet | % w/wt |
| Co-Processed Erythritol[1] | 2240.0 | 129.47 | 44.8 |
| Maltodextrin | 1210.0 | 69.94 | 24.2 |
| Encapsulated Acetaminophen | 1540.0 | 89.01 | 30.8 |
| Sucralose USP | 5.00 | 0.29 | 0.1 |
| Berry Flavor | 10.00 | 0.58 | 0.2 |
| Total | 5000.0 | 289.0 | 100.0 |
| b: Physical Properties of tablets from Example 1 | | | |
| Average tablet weight (mg) | 330 | | |
| Tablet Thickness (mm) | 4.29 | | |
| Approximate tablet density (g/cc) | 0.61 | | |
| Oral disintegration time | 13 sec | | |
| Friability (% loss after 10 drops) | 0.05 | | |
| Hardness | 476 g | | |

[1]Available from Corn Products in Westchester, IL as Erysta ® 3656 DC (80% erythritol)

First, the sucralose, maltodextrin, encapsulated acetaminophen, and flavor were placed together into a 1 cubic foot V-blender. The Erythritol was passed through a 20 mesh screen and added to the V-blender. The mixture was then blended end-over-end for approximately 5 minutes at 25 RPM and discharged into a lined drum. The blend was filled into ½ inch round dies and sintered at a radio frequency of 27 MHz for approximately 2 seconds to form an orally disintegrating tablet.

Example 2

Manufacture of Orally Disintegrating Tablet Containing Erythritol and Acetaminophen The acetaminophen powder blend for an orally disintegrating tablet, containing the ingredients of Table 2, was manufactured as follows:

TABLE 2 a: Acetaminophen Powder Blend Formulation

| Ingredient | G/Batch | mg/Tablet | % w/wet |
|---|---|---|---|
| Co-Processed Erythritol | 2465.0 | 134.59 | 49.3 |
| Maltodextrin | 1330.0 | 72.62 | 26.6 |
| Encapsulated Acetaminophen | 1185.0 | 64.70 | 23.7 |
| Sucralose USP | 10.0 | 0.55 | 0.2 |
| Berry Flavor | 10.0 | 0.55 | 0.2 |
| Total | 5000.0 | 273.0 | 100.0 | b: Physical Properties of tablets from Example 2

| Average tablet weight (mg) | 310 |
|---|---|
| Tablet Thickness (mm) | 4.38 |
| Approximate tablet density (g/cc) | 0.53 |
| Oral disintegration time | 12 sec |
| Friability (% loss after 10 drops) | 1.1 |
| Hardness | 464 g |

First, the sucralose, maltodextrin, encapsulated acetaminophen, and flavor were placed together into a 1 cubic foot V-blender. The Erythritol was passed through a 20 mesh screen and added to the V-blender. The mixture was then blended end-over-end for approximately 5 minutes at 25 RPM and discharged into a lined drum. The blend was filled into ½ inch round dies and sintered at a radio frequency of 27 MHz for approximately 2 seconds to form an orally disintegrating tablet.

Example 3

Manufacture of Orally Disintegrating Tablet Containing Erythritol and Famotidine The famotidine powder blend for an orally disintegrating tablet, containing the ingredients of Table 3, was manufactured as follows:

TABLE 3

Famotidine Powder Blend Formulation

| Ingredient | G/Batch | mg/Tablet | % per Tablet |
|---|---|---|---|
| Co-Processed Erythritol | 12.06 | 83.82 | 60.3 |
| Maltodextrin | 6.54 | 45.45 | 32.7 |
| Famotidine | 1.40 | 9.73 | 7.0 |
| Total | 20.0 | 139.0 | 100.0 |

TABLE 3-continued b: Physical Properties of tablets from Example 3

| Average tablet weight (mg) | 139 |
|---|---|
| Tablet Thickness (mm) | 5.1 |
| Approximate tablet density (g/cc) | 0.23 |
| Oral disintegration time | 9 sec |
| Friability (% loss after 10 drops) | 1.7% |
| Hardness | 200 g |

The maltodextrin and famotidine were placed together into a plastic bag. The Erythritol was passed through a 20 mesh screen and added to the bag. The mixture was then blended end-over-end manually for approximately 5 minutes. The blend was filled into ½ inch round dies and sintered at a radio frequency of 27 MHz for approximately 2 seconds to form an orally disintegrating tablet.

Example 4

Manufacture of Orally Disintegrating Tablet Containing Erythritol and Acetaminophen The acetaminophen powder blend for an orally disintegrating tablet, containing the ingredients of Table 4, was manufactured as follows:

TABLE 4 a: Acetaminophen Powder Blend Formulation

| Ingredient | G/Batch | mg/Tablet | % per Tablet |
|---|---|---|---|
| Erythritol | 35.75 | 97.60 | 35.75 |
| Maltodextrin (DE 10) | 29.25 | 79.85 | 29.25 |
| Encapsulated Acetaminophen | 35.0 | 95.55 | 35.0 |
| Total | 100.0 | 273.0 | 100.0 | b: Physical Properties of tablets from Example 4

| Average tablet weight (mg) | 246 |
|---|---|
| Tablet Thickness (mm) | 3.81 |
| Approximate tablet density (g/cc) | 0.54 |
| Oral disintegration time | 10 sec |
| Friability (% loss after 10 drops) | 0.06 |
| Hardness | 410 g |

The maltodextrin and encapsulated acetaminophen were placed together into a plastic bag. The Erythritol was passed through a 20 mesh screen and added to a plastic bag. The mixture was then blended end-over-end manually for approximately 5 minutes. The blend was filled into ½ inch round dies and sintered at a radio frequency of 27 MHz for approximately 2 seconds to form an orally disintegrating tablet.

Example 5

Manufacture of Orally Disintegrating Tablet Containing Dextrose Monohydrate and Acetaminophen The acetaminophen powder blend for an orally disintegrating tablet, containing the ingredients of Table 4, was manufactured as follows:

TABLE 5 a: Acetaminophen and Dextrose Monohydrate Powder Blend Formulation

| Ingredient | G/Batch | mg/Tablet | % per Tablet |
|---|---|---|---|
| Dextrose Monohydrate | 41.25 | 112.61 | 41.25 |
| Maltodextrin | 33.75 | 92.14 | 33.75 |

TABLE 5-continued

| Encapsulated Acetaminophen | 25.00 | 68.25 | 25.00 |
|---|---|---|---|
| Total | 100.0 | 273.0 | 100.0 | b: Physical Properties of tablets from Example 5

| | |
|---|---|
| Average tablet weight (mg) | 347 |
| Tablet Thickness (mm) | 3.7 |
| Approximate tablet density (g/cc) | 0.38 |
| Oral disintegration time | 10 sec |
| Friability (% loss after 10 drops) | 1.4 |
| Hardness | 271 g |

The maltodextrin and encapsulated acetaminophen were placed together into a 1 cubic foot V-blender. The Dextrose Monohydrate was passed through a 20 mesh screen and added to a plastic bag. The mixture was then blended end-over-end manually for approximately 5 minutes. The blend was filled into ½ inch round dies and sintered at a radio frequency of 27 MHz for approximately 2 seconds to form an orally disintegrating tablet.

Example 6

Manufacture of Orally Disintegrating Tablet Containing Mannitol and Acetaminophen The acetaminophen powder blend for an orally disintegrating tablet, containing the ingredients of Table 6, was manufactured as follows:

TABLE 6 a: Acetaminophen and Mannitol Powder Blend Formulation

| Ingredient | G/Batch | mg/Tablet | % per Tablet |
|---|---|---|---|
| Mannitol (Spray Dried, 120 microns)[1] | 41.25 | 112.61 | 41.25 |
| Maltodextrin | 33.75 | 92.14 | 33.75 |
| Encapsulated Acetaminophen | 25.00 | 68.25 | 25.00 |
| Total | 100.0 | 273.0 | 100.0 | b: Physical Properties of tablets from Example 6

| | |
|---|---|
| Average tablet weight (mg) | 309 |
| Tablet Thickness (mm) | 6.6 |
| Approximate tablet density (g/cc) | 0.35 |
| Oral disintegration time | 10 sec |
| Friability (% loss after 10 drops) | 2.0 |
| Hardness | 202 g |

[1]Available from SPI Pharma in Lewes, DE as Mannogem EZ ®.

The maltodextrin and encapsulated acetaminophen were placed together into a plastic bag. The Mannitol was passed through a 20 mesh screen and added to the plastic bag. The mixture was then blended end-over-end manually for approximately 5 minutes. The blend was filled into ½ inch round dies and sintered at a radio frequency of 27 MHz for approximately 2 seconds to form an orally disintegrating tablet.

Example 7

Manufacture of Placebo Orally Disintegrating Tablet Containing Maltodextrin and Erythritol The placebo powder blend for an orally disintegrating tablet, containing the ingredients of Table 7a, was manufactured as follows: The direct compression erythritol was delumped by passing through a 20 mesh hand screen. The de-lumped erythritol and maltrodextrin were blended in a 1 cubic ft V-blender for 5 minutes.

TABLE 7a

Maltodextrin/Erythritol Powder Blend Formulation

| Ingredient | G/Batch | % w/w |
|---|---|---|
| Co-processed Erythritol | 2742 | 54.84 |
| Maltodextrin | 2258 | 45.16 |
| Total | 5000 | 100 |

The blend was filled into ½ inch round dies and sintered at a radio frequency of 27 MHz for approximately 1.5 seconds to form an orally disintegrating tablet having the properties shown in Table 7b.

TABLE 7b

Physical Properties of tablets from Example 7

| | |
|---|---|
| Average tablet weight (mg) | 260 |
| Approximate tablet density (g/cc) | 0.38 |
| Oral disintegration time | 13-24 sec |
| Friability (% loss after 10 drops) | 2.0 |

Example 8

Comparative Example: Manufacture of Orally Disintegrating Tablets

The orally disintegrating tablet of Example 4 of US Patent Application No. 2011/0071184, containing the ingredients of Table 8a, was manufactured using radiofrequency energy as set forth in therein.

TABLE 8a

Dextrose/PEG/Maltodextrin Powder Blend Formulation

| Ingredient | G/Batch | % w/w |
|---|---|---|
| Dextrose Monohydrate, NF | 141.5 | 71 |
| Orange Flavor | 0.66 | 0.3 |
| Vanilla Flavor | 0.88 | 0.4 |
| Yellow Colorant | 0.31 | 0.2 |
| Sucralose NF | 0.44 | 0.2 |
| Citric Acid Anhydrous USP | 3.18 | 1.6 |
| Polyethylene Glycol 4000 | 17.65 | 8.8 |
| Maltodextrin | 35.35 | 17.7 |
| Total | 199.97 | 100 |

The above formulation thus had a concentration of maltodextrin of less than 20%, by weight, of the tablet, in addition to a high level of polyethylene glycol. The resulting orally disintegrating tablet had the properties shown in Table 8b.

TABLE 8b

Physical Properties of tablets from Example 9

| | |
|---|---|
| Average tablet weight (mg) | 310 |
| Approximate tablet density (g/cc) | 0.667 |
| Oral disintegration time | 5 sec |
| Friability (% loss after 5 drops) | 100 |

As is evidenced above, the resulting tablets had a friability of 100%, as compared to the friability of the tablets set forth in Examples 1-7, which had friabilities of less than 1.7%, thus indicating an unexpected benefit of the formulations of the present invention.

Example 9

Manufacture of Orally Disintegrating Tablet Containing Mannitol and Acetaminophen The acetaminophen powder blend for an orally disintegrating tablet, containing the ingredients of Table 9, was manufactured as follows:

TABLE 9 a: Acetaminophen and Mannitol Powder Blend Formulation

| Ingredient | G/Batch | mg/Tablet | % per Tablet |
|---|---|---|---|
| Mannitol (Spray Dried, 120 microns)[1] | 87.5 | 175 | 55.4 |
| Maltodextrin (DE 6) | 26 | 52 | 16.5 |
| Encapsulated Acetaminophen | 44 | 88 | 27.8 |
| Sucralose NF | 0.2 | 0.4 | 0.1 |
| Flavor | 0.3 | 0.6 | 0.2 |
| Total | 158 | 316 | 100 | b: Physical Properties of tablets from Example 9

| | |
|---|---|
| Average tablet weight (mg) | 322 |
| Tablet Thickness (mm) | 4.1 |
| Approximate tablet density (g/cc) | 0.63 |
| Oral disintegration time (sec) | 9 |
| Friability (% loss after 15 drops) | 3.1 |

[1]Available from SPI Pharma in Lewes, DE as Mannogem EZ ®.

The maltodextrin and encapsulated acetaminophen were placed together into a 32 ounce glass jar. The Mannitol was passed through a 20 mesh screen and added to the glass jar. The mixture was then blended using a Turbula Model T2C mixer for approximately 5 minutes. The blend was filled into ½ inch round dies and sintered at a radio frequency of 27 MHz for approximately 3 seconds to form an orally disintegrating tablet.

Example 10

Manufacture of Orally Disintegrating Tablet Containing Dextrose and Acetaminophen The acetaminophen powder blend for an orally disintegrating tablet, containing the ingredients of Table 10, was manufactured as follows:

TABLE 10 a: Acetaminophen and Dextrose Powder Blend Formulation

| Ingredient | G/Batch | mg/Tablet | % per Tablet |
|---|---|---|---|
| Dextrose Monohydrate[1] | 82 | 127 | 41 |
| Maltodextrin (DE 18) | 62 | 87 | 28 |
| Encapsulated Acetaminophen | 56 | 96 | 31 |
| Total | 200 | 310 | 100 | b: Physical Properties of tablets from Example 10

| | |
|---|---|
| Average tablet weight (mg) | 310 |
| Tablet Thickness (mm) | 4.4 |
| Approximate tablet density (g/cc) | 0.56 |
| Oral disintegration time (sec) | 11 |
| Friability (% loss after 15 drops) | 4.2 |

[1]Available from Roquette Corporation as Dextrose Monohydrate ST ®.

The maltodextrin and encapsulated acetaminophen were placed together into a 32 ounce glass jar. The dextrose was added to the glass jar. The mixture was then blended using a Turbula Model T2C mixer for approximately 5 minutes. The blend was filled into ½ inch round dies and sintered at a radio frequency of 27 MHz for approximately 2.5 seconds to form an orally disintegrating tablet.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A tablet comprising at least one first material, at least one second material, and at least one pharmaceutically active agent, wherein:
    (a) said first material comprises maltodextrin;
    (b) said second material is a sugar or sugar alcohol;
    (c) said tablet comprises from at least 15% to about 45%, by weight, of said first material and from about 20% to about 64%, by weight, of said second material;
    (d) the combined weight of said at least one first material and said at least one second material comprises at least 60%, by weight, of said tablet;
    (e) said tablet has a friability of less than about 5%;
    (f) said tablet has a density less than about 0.8 g/cc;
    (g) said tablet disintegrates in the mouth when placed on the tongue in less than about 30 seconds; and
    (h) said tablet comprises less than 5%, by weight, of a polyethylene glycol.

2. A tablet of claim 1, wherein said tablet comprises at least 20%, by weight, of said first material.

3. A tablet of claim 1, wherein said at least one first material has a bulk density of less than 0.2 g/cc.

4. A tablet of claim 1, wherein said at least one second material comprises erythritol.

5. A tablet of claim 1, wherein the combined weight of said at least one first material, said at least one second material, and said at least one pharmaceutically active agent comprises at least 90%, by weight, of said tablet.

6. A tablet of claim 5 wherein said tablet comprises from about 20% to about 45%, by weight, of said first material.

7. A tablet of claim 1, wherein said at least one pharmaceutically active agent are comprised within polymer-coated particles, and said tablet comprises at least 15%, by weight, of said particles.

8. A tablet of claim 1, wherein said tablet does not comprise a polyethylene glycol.

9. A tablet of claim 1, wherein at least 90%, by weight, of the tablet is comprised of material having a melting point greater than 80 C.

10. A tablet of claim 1, wherein the peak penetration resistance at the center of the major face of the tablet is from about 50 to about 600 grams.

11. A tablet of claim 1, wherein said tablet meets the criteria for orally disintegrating tablets as defined by the draft Food & Drug Administration guidance, as published April, 2007.

12. A tablet of claim 1, wherein said tablet comprises from about 39 to about 56%, by weight, of said at least one second material.

13. A tablet of claim 1, wherein said tablet comprises from about 10 to about 40%, by weight, of particles comprising said pharmaceutically active agent.

14. A tablet of claim 1, wherein said tablet disintegrates in the mouth when placed on the tongue in less than about 15 seconds.

15. A tablet of claim 1, wherein the combined weight of said at least one first material, said at least one second material, and said at least one pharmaceutically active agent comprises at least 95%, by weight, of said tablet.

* * * * *